(12) United States Patent
Kleinberg et al.

(10) Patent No.: US 6,257,730 B1
(45) Date of Patent: Jul. 10, 2001

(54) DRAPE FOR A SURGICAL MICROSCOPE WITH ANTI-HALATION WINDOW

(75) Inventors: Larry K. Kleinberg, Chesterfield; Nicholas E. John, St. Louis, both of MO (US)

(73) Assignee: Global Surgical Corporation, St. Louis, MO (US)

( * ) Notice: Subject to any disclaimer, the term of this patent is extended or adjusted under 35 U.S.C. 154(b) by 0 days.

(21) Appl. No.: 09/449,405

(22) Filed: Nov. 26, 1999

Related U.S. Application Data

(63) Continuation of application No. 09/006,120, filed on Jan. 12, 1998, now abandoned, which is a continuation-in-part of application No. 08/850,939, filed on May 5, 1997, now abandoned.

(51) Int. Cl.[7] ............................ G02B 27/00; G03B 11/04
(52) U.S. Cl. ...................... 359/600; 359/601; 359/608; 359/510
(58) Field of Search .................................. 359/507–510, 359/511–513, 600–601, 611–614, 894–895, 368, 376, 377; 206/316.1; 600/122–123, 158

(56) References Cited

U.S. PATENT DOCUMENTS

| 3,402,981 | * | 9/1968 | Cardone | 359/613 |
| 3,796,477 | * | 3/1974 | Geraci | 359/600 |
| 5,311,358 |   | 5/1994 | Pederson et al. | 359/510 |
| 5,386,817 |   | 2/1995 | Jones | 128/4 |
| 5,467,223 |   | 11/1995 | Cleveland, Jr. et al. | 359/510 |
| 5,526,181 | * | 6/1996 | Kunick et al. | 359/613 |
| 5,608,574 |   | 3/1997 | Heinrich | 359/510 |

* cited by examiner

Primary Examiner—Thong Nguyen
(74) Attorney, Agent, or Firm—Harness, Dickey & Pierce

(57) ABSTRACT

A drape for a surgical microscope comprising a flexible cover for separating the microscope from the surgical field. There is a frame in the cover adapted to be secured over the objective lens of the microscope, and a dome-shaped protective window in the frame. The window is oriented so that when the frame is secured over the objective lens the dome extends toward or away from the objective lens to minimize reflection of light from the protective window into the optical path of the microscope.

24 Claims, 4 Drawing Sheets

DRAPE FOR A SURGICAL MICROSCOPE WITH ANTI-HALATION WINDOW

CROSS-REFERENCED TO RELATED APPLICATION

This application is a continuation of U.S. patent application Ser. No. 09/006,120, filed Jan. 12, 1998, (now abandoned), which is a continuation-in-part of U.S. patent application Ser. No. 08/850,939, filed May 5, 1997 (now abandoned).

FIELD OF THE INVENTION

This invention relates to drapes for surgical microscopes.

BACKGROUND OF THE INVENTION

Surgical microscopes are typically covered with a disposable drape to prevent contamination of the microscope from the patient or contamination of the patient from the microscope. The drape comprises a flexible cover having a flat transparent window therein aligned with the objective lens of the microscope.

In many surgical microscopes the objective lens transmits light from a light source to the surgical site to illuminate the surgical site, and the objective lens also transmits the image of the surgical site to the optical path of the microscope.

The flat window in the drape allows light form the objective lens to pass to the surgical site, and it allows the image to pass from the surgical site to the objective lens. One problem encountered with conventional drapes is that the flat window will reflect some of the light that is transmitted from the objective lens back to the objective lens and into the optical or viewing path of the microscope. The reflected light impairs the image of the surgical site due to a phenomenon called halation. Anti reflective coatings can be applied to the window, but even with antireflective coatings, a substantial amount of light is reflected into the optical or viewing path. U.S. Pat. No. 5,608,574, incorporated herein by reference, discloses a flat slanted window. Tilting the window can also reduce the amount of light reflected into the optical or viewing path, but this introduces a distortion or astigmatism into the viewed image. (An astigmatism is a defocusing of the image along one axis). Also the slant of the drape lens reduces the clearance between the microscope and the surgical field, which may cause the surgeon to compromise and use a longer lens to allow adequate working space between the microscope and the surgical field. Some surgeons remove the window to avoid these problems, compromising the effectiveness of the drape.

Another problem experienced with flat windows is that to save cost these windows are made of molded plastic, and flat molded plastic parts tend to have irregular peaks and valleys on their surfaces. This surface irregularity introduces additional distortion into the image, and because it is essentially random, it is difficult for the eye to accommodate, resulting in a very poor image.

SUMMARY OF THE INVENTION

The drape of the present invention is adapted to be installed over a surgical microscope to isolate the surgical microscope from the surgical field. Generally, the drape of the present invention comprises a cover for covering a surgical microscope having a window therein adapted to be aligned with the objective lens of the microscope. However, the window is convexly curved. The convex configuration of the window reduces the amount of light reflected from the window back to the objective lens.

When properly installed on a surgical microscope, the drape of the present invention isolates the microscope from the surgical field. The window allows light form the objective lens to pass to the surgical site and allows the image to pass from the surgical site to the objective lens. The convex configuration of the window reduces the amount of reflected light received by the objective lens, reducing halation.

Another benefit of the concave/convex curved configuration of the window is that even if it is made out of molded plastic, any distortions tend to be in the radial direction. This does not affect the imagery of the optical surface, although it does affect the curvature and ultimately the magnifying power. Aberrations introduced by this type of shape are in a controlled direction and more easily accommodated by the eye.

Still another possible benefit of the concave/convex configuration of the window is that the shape of the window can be designated to cooperate with the optics of the microscope to increase the optical erformance of the microscope.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
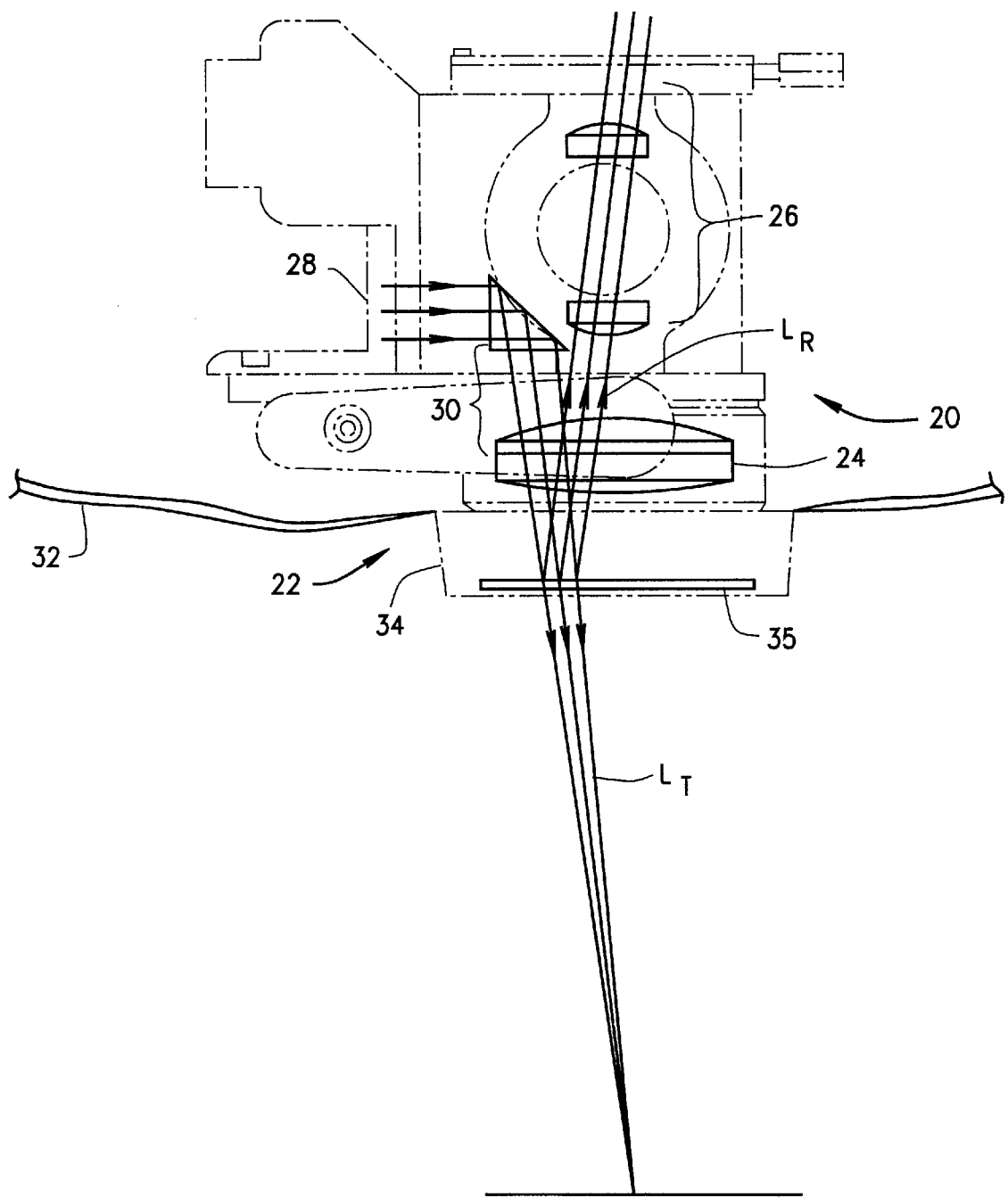
FIG. 1 is a schematic diagram of the light paths in a microscope with a drape with a conventional window.

A surgical microscope, indicated generally as 20, is shown in FIG. 1 with a conventional drape 22 for isolating the surgical microscope from the surgical field. As shown in FIG. 1, a surgical microscope typically includes an objective lens 24, an optical or viewing path 26, optically aligned with the objective lens for receiving the image of the surgical site through the objective lens, and a light source 28 and illumination path 30 for transmitting light to the surgical site through the objective lens. The drape 22 comprises a cover 32 with a frame 34 having a flat window 35 aligned with the objective lens 24 of the microscope 20. The cover 32 is typically made of a plastic sheet material. The frame 34 is typically made from a rubber or elastomer to fit over the objective lens 24 of the microscope 20. The window 35 is typically made of a transparent plastic. As shown in FIG. 1, light from the light source passes through the illumination path, through the objective lens 24. The flat window 35 transmits most of this light $L_T$ to the surgical site, but the flat window 35 reflects some of this light LR into the optical or viewing path 26. While illustrated in two dimensions in FIG. 1, the reflection is in three dimensions, causing incoherent light to appear in the image. This light impairs the image from the surgical site due to an effect known as "halation."

Figure 2:
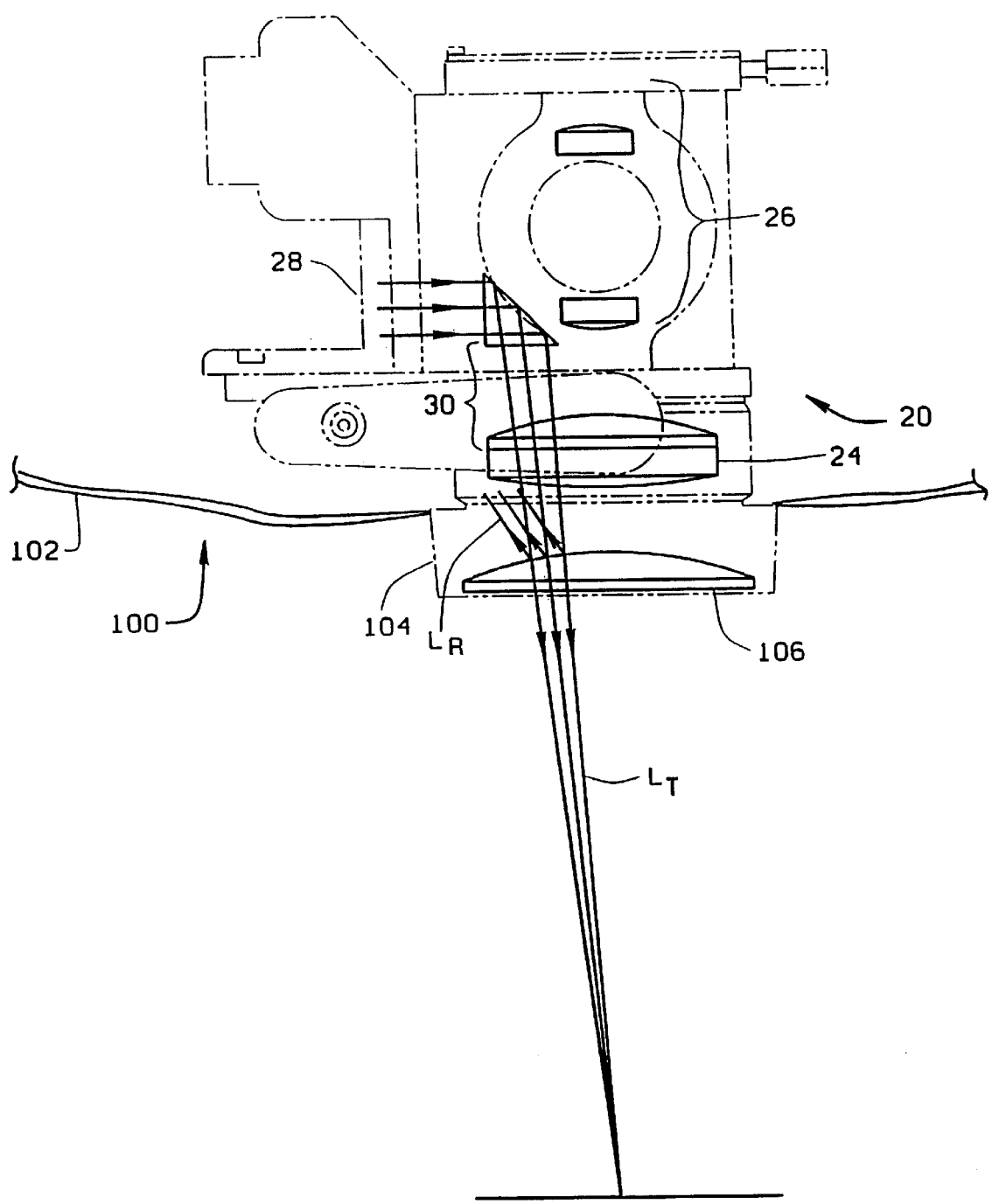
FIG. 2 is a schematic diagram of the light paths in a surgical microscope with a first embodiment of a drape constructed according to the principles of this invention.
Figure 3:
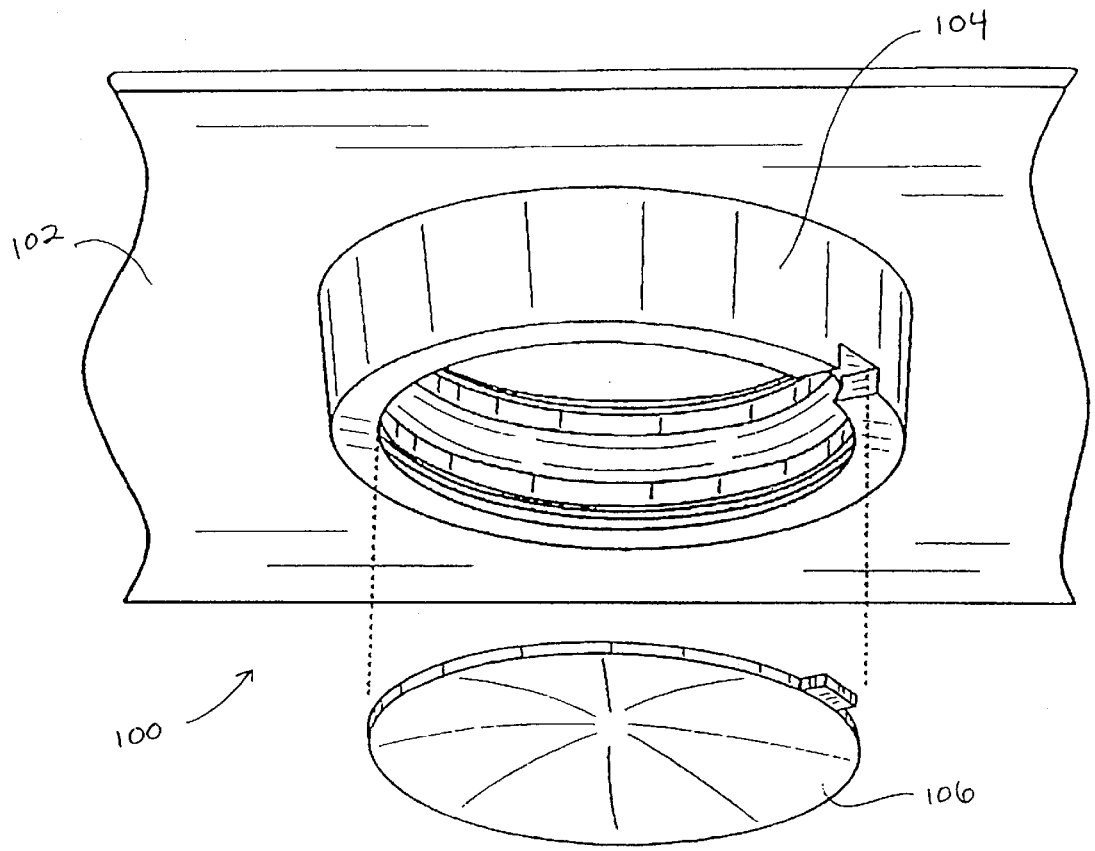
FIG. 3 is a perspective view of the first embodiment of a drape constructed according to the principles of this invention, with the window removed to show detail.
Figure 4:
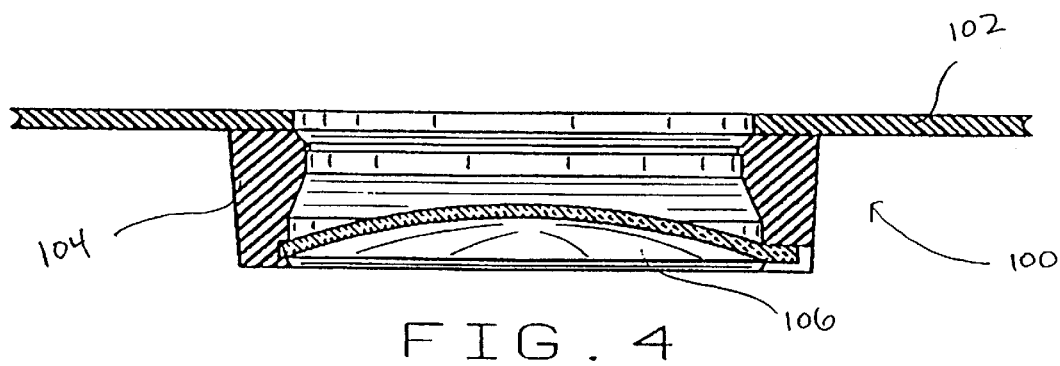
FIG. 4 is a cross-sectional view of the first embodiment of the drape.

A first embodiment of a drape constructed according to the principles of the present invention is indicated generally as 100 in FIGS. 2, 3 and 4. The drape 100 comprises a cover 102 having a frame 104 therein. The cover 102 may be made of a flexible plastic sheet material, and the frame 104 may be made from a rubber or elastomeric material. A convexly curved dome-shaped window 106 is mounted in the frame, so that when the drape 100 is installed on a microscope, the dome is oriented toward the objective lens 22. The window 106 is preferably made of transparent plastic. As shown in FIG. 2, the dome-shaped window 106 transmits most of the light $L_T$ to the surgical site, but the window does reflect some of the light $L_R$. However, because of the domed shape of the window, less of the reflected light $L_R$ is reflected into the optical or viewing path 26, than with prior art flat windows. Thus, the "halation" effect is reduced and the quality of the image from the surgical site is improved.

Moreover, because of the concave/convex shape of the window 106, the window can be inexpensively made from molded plastic The concave/convex shape of the window orients the majority of distortions in the molded plastic, such that the human eye can accommodate and "correct" for any distortion introduced better than the eye can accommodate and "correct" for the type of random distortion introduced by a flat molded plastic window.

Furthermore, because of the concave/convex shape of the window 106 it can be designed to actually be an optical element cooperating with the optics in the microscope. Thus rather than an optically neutral flat window used in prior art drapes, the window 106 can be made with optical power to enhance the optics of the microscope.

The dome shaped window can be configured to provide positive magnification, negative magnification, or to not change the magnification of the microscope.

Figure 5:
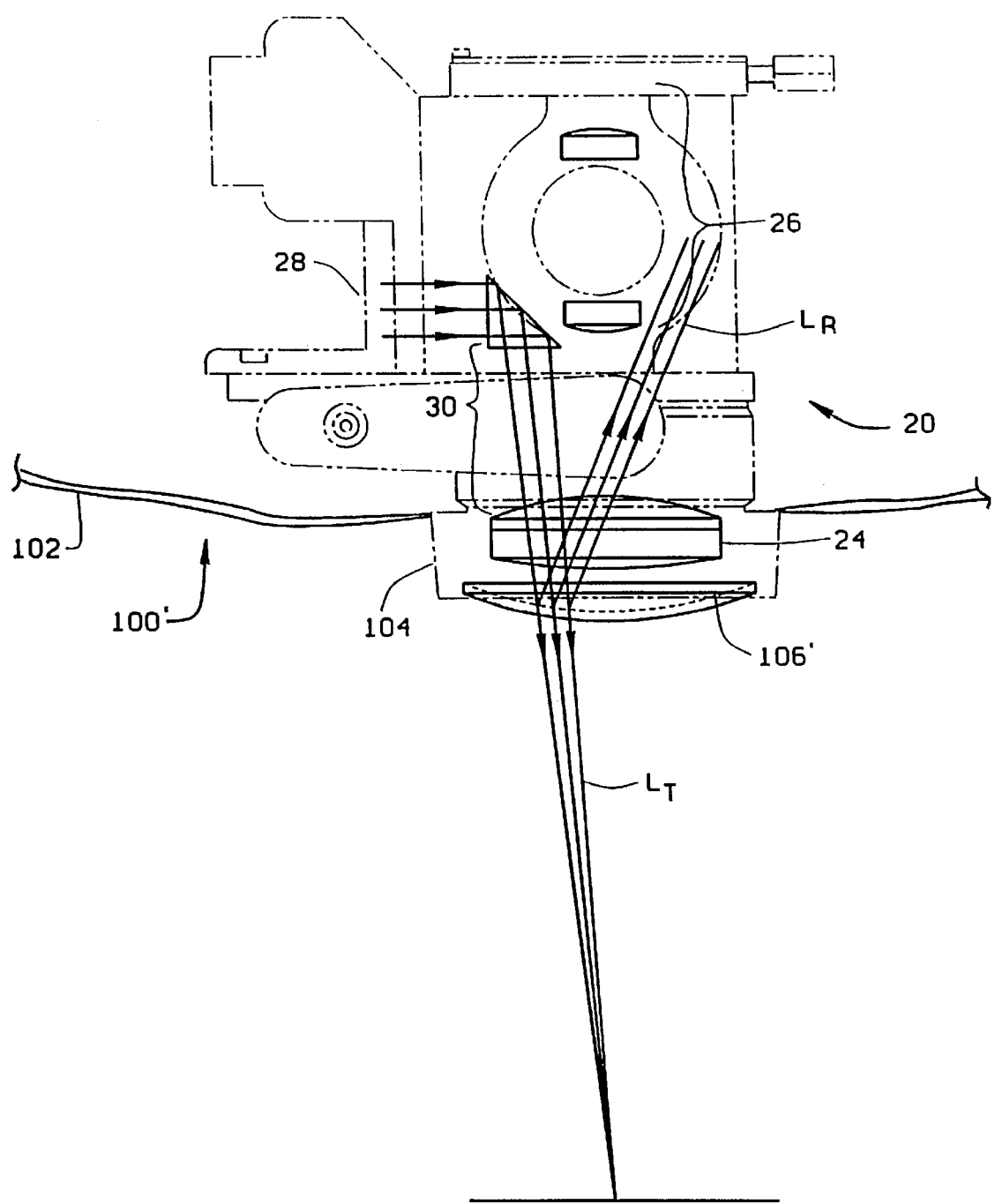
FIG. 5 is a schematic diagram of the light paths in a surgical microscope with a second embodiment of a drape constructed according to the principles of this invention.

A second embodiment of a drape constructed according to the principles of the present invention is indicated generally as 100 in FIG. 5. The drape 100' is similar in construction to drape 100, except that the window 106' is oriented away from the objective lens of the microscope, rather than toward it like window 106 of drape 100. As shown in FIG. 5, the dome-shaped window 106' transmits most of the light $L_T$ to the surgical site, but the window reflects some light $L_R$. However because of the domed shape of the window 106', less of the light is reflected into the optical or viewing path 26, than with the prior art flat windows.

What is claimed is:

1. A drape for a surgical microscope with an optical path having optics including an object lens, the drape comprising a flexible cover for separating the microscope from a surgical field, a frame in the cover adapted to be secured to the object lens of the microscope, and a dome-shaped protective window, having a concave surface on one side and a convex surface on the other side, in the frame oriented so that when the frame is secured over the objective lens, the dome configuration reduces reflection of light from the protective window into the optical path of the microscope.

2. The drape according to claim 1 wherein the window is oriented with the dome shape extending toward the objective lens.

3. The drape according to claim 1 wherein the window is oriented with the dome shape extending away from the objective lens.

4. The drape according to claim 1 wherein the protective window is made from molded plastic.

5. The drape according to claim 1 wherein the protective window has optical properties that cooperate with the optics of the microscope to enhance a viewed image.

6. The drape according to claim 5 wherein the protective window has positive magnification.

7. The drape according to claim 5 wherein the protective window has negative magnification.

8. The drape according to claim 5 wherein the protective window does not change the magnification of the microscope on which it is installed.

9. In combination with a surgical microscope of the type with an optical path having optics including an object lens and a light source that projects through the object lens to a surgical field for illuminating the surgical field, a drape to be fit over the microscope to separate the microscope from the surgical field, the drape having a frame adapted to be secured on the microscope in alignment with the object lens, and a dome-shaped protective window in the frame, having a concave surface on one side and a convex surface on the other side, to reduce reflection of light from the light source into the optical path of the microscope by the protective window.

10. The combination according to claim 9 wherein the window is oriented with the dome shape extending toward the objective lens.

11. The combination according to claim 9 wherein the window is oriented with the dome shape extending away from the objective lens.

12. The combination according to claim 9 wherein the protective window is made from molded plastic.

13. The combination according to claim 9 wherein the protective window as optical properties that cooperate with the optics of the microscope to enhance a viewed image.

14. The combination according to claim 13 wherein the protective window has positive magnification.

15. The combination according to claim 13 wherein the protective window has negative magnification.

16. The combination according to claim 13 wherein the protective window does not change the magnification of the microscope on which it is installed.

17. An improved drape for a surgical microscope with an optical path having optics including an object lens and a light source that projects through the object lens to a surgical field for illuminating the surgical field, the drape of the type comprising a cover, a frame in the cover for mounting on the microscope in alignment with the object lens, and a transparent protective window in the frame allowing light to pass through the drape, the improvement comprising convexly curving the protective window on the microscope side of the drape to minimize reflection of the light from the light source into the optical path of the microscope by the protective window, and concavely curving the opposite side of the window.

18. The improved drape according to claim 17 wherein the protective window is made from molded plastic.

19. The improved drape according to claim 18 wherein the window is oriented with the dome shape extending toward the objective lens.

20. The improved drape according to claim 18 wherein the window is oriented with the dome shape extending away from the objective lens.

21. The improved drape according to claim 18 wherein the protective window has optical properties that cooperate with the optics of the microscope to enhance the viewed image.

22. The improved drape according to claim 21 wherein the protective window has positive magnification.

23. The improved drape according to claim 21 wherein the protective window has negative magnification.

24. The improved drape according to claim 21 wherein the protective window does not change the magnification of the microscope on which it is installed.

* * * * *